(12) United States Patent
Yerramilli et al.

(10) Patent No.: US 8,778,699 B2
(45) Date of Patent: Jul. 15, 2014

(54) DETECTION OF DEGRADATION PRODUCTS OF CANINE NT-PROBNP

(75) Inventors: Mahalakshmi Yerramilli, Falmouth, ME (US); Michael Atkinson, Gorham, ME (US); Murthy V. S. N. Yerramilli, Falmouth, ME (US)

(73) Assignee: Idexx Laboratories, Inc., Westbrook, ME (US)

( * ) Notice: Subject to any disclaimer, the term of this patent is extended or adjusted under 35 U.S.C. 154(b) by 123 days.

(21) Appl. No.: 13/198,092

(22) Filed: Aug. 4, 2011

(65) Prior Publication Data

US 2012/0034710 A1 Feb. 9, 2012

Related U.S. Application Data

(60) Provisional application No. 61/370,712, filed on Aug. 4, 2010.

(51) Int. Cl.
| | | |
|---|---|---|
| G01N 33/74 | (2006.01) | |
| G01N 33/543 | (2006.01) | |
| G01N 33/577 | (2006.01) | |
| C07K 16/26 | (2006.01) | |
| G01N 33/68 | (2006.01) | |
| C12P 21/08 | (2006.01) | |
| G01N 33/545 | (2006.01) | |

(52) U.S. Cl.
CPC ............... *G01N 33/74* (2013.01); *C07K 16/26* (2013.01); *G01N 33/6848* (2013.01); *G01N 2800/52* (2013.01); *G01N 2800/7019* (2013.01); *G01N 2800/325* (2013.01); *G01N 2800/50* (2013.01); *G01N 33/543* (2013.01); *G01N 33/577* (2013.01); *G01N 2800/32* (2013.01); *G01N 2333/58* (2013.01); *G01N 33/545* (2013.01)
USPC .......... 436/518; 435/7.1; 435/7.92; 435/7.93; 435/7.94; 436/501; 436/514; 436/528; 436/531; 436/548; 436/87; 530/387.9; 530/388.24; 530/389.2; 530/391.1; 530/391.3

(58) Field of Classification Search
CPC ..... C07K 16/26; G01N 33/53; G01N 33/537; G01N 33/543; G01N 33/545; G01N 33/577; G01N 33/6848; G01N 33/74; G01N 2333/58; G01N 2800/32; G01N 2800/325; G01N 2800/50; G01N 2800/52; G01N 2800/7019
USPC .......... 435/7.1, 7.92, 7.93, 7.94, 69.3, 70.21, 435/287.2, 287.9, 975; 436/501, 514, 518, 436/528, 531, 548, 8, 15, 87, 811, 817; 530/388.24, 389.2, 391.1, 391.3, 530/387.9; 422/425, 430
See application file for complete search history.

(56) References Cited

U.S. PATENT DOCUMENTS

| | | |
|---|---|---|
| 3,817,837 A | 6/1974 | Rubenstein et al. |
| 3,996,345 A | 12/1976 | Ullman et al. |
| 5,114,923 A | 5/1992 | Seilhamer et al. |
| 5,185,243 A | 2/1993 | Ullman et al. |
| 5,498,524 A | 3/1996 | Hall |
| 5,726,010 A | 3/1998 | Clark |
| 5,786,163 A | 7/1998 | Hall |
| 6,489,309 B1 | 12/2002 | Singh et al. |
| 6,586,396 B1 | 7/2003 | Seilhamer et al. |
| 7,264,938 B2 | 9/2007 | Borgya et al. |
| 7,264,939 B2 | 9/2007 | Borgya et al. |
| 7,553,937 B2 | 6/2009 | Pau et al. |
| 2003/0069186 A1 | 4/2003 | Burnett et al. |
| 2004/0018577 A1 | 1/2004 | Emerson Campbell et al. |
| 2004/0096920 A1 | 5/2004 | Davey et al. |
| 2006/0051825 A1 | 3/2006 | Buechler et al. |
| 2006/0110775 A1 | 5/2006 | Borgya et al. |
| 2006/0110776 A1 | 5/2006 | Borgya et al. |
| 2007/0059767 A1 | 3/2007 | Karl et al. |
| 2007/0161041 A1 | 7/2007 | Woloszczuk et al. |
| 2009/0170136 A1 | 7/2009 | Woloszczuk et al. |
| 2010/0075429 A1 | 3/2010 | Hess et al. |
| 2010/0136590 A1 | 6/2010 | Woloszczuk et al. |
| 2010/0203560 A1 | 8/2010 | Tamm et al. |

FOREIGN PATENT DOCUMENTS

| | | | |
|---|---|---|---|
| AU | 200025451 | * | 8/2000 |
| EP | 0648228 | | 11/1998 |
| EP | 1016867 | | 1/2006 |
| JP | 2002-272458 | | 9/2002 |
| WO | 00/35951 | | 6/2000 |
| WO | 00/45179 | | 8/2000 |
| WO | 00/71576 | | 11/2000 |
| WO | 02/059567 | | 8/2002 |
| WO | 03/087819 | | 10/2003 |
| WO | 2004/094460 | * | 11/2004 |
| WO | 2008056034 | | 5/2008 |

OTHER PUBLICATIONS

Oyama et al., 2008. Clinical utility of serum N-terminal pro-B-type natriuretic peptide concentration for identifying cardiac disease in dogs and assessing disease severity. J. Am. Vet. Med. Assoc. 232: 1496-1503.*
Asano et al., "Plasma atrial and brain natriuretic peptide levels in dogs with congestive heart failure" J. Vet. Med. Sci.; 61(5): 523-9 (1999).
Biondo et al., "Immunohistochemistry of atrial and brain natriuretic peptides in control cats and cats with hypertrophic cardiomyopathy"; Vet. Pathol.; 40: 501-6 (2003).
Boswood, et al., "The diagnostic accuracy of different natriuretic peptides in the investigation of canine cardiac disease"; J. Small Animal Practice; 49: 26-32 (2008).
Goetze, "Biochemistry of pro-B-type natriuretic peptide-derived peptides: the endocrine heart revisited.", Clin. Chem.; 50: 1503-10 (2004).

(Continued)

*Primary Examiner* — Gail R Gabel
*Assistant Examiner* — James L Grun
(74) *Attorney, Agent, or Firm* — McDonnell Boehnen Hulbert & Berghoff LLP

(57) ABSTRACT

A method for determining the amount of NT-proBNP in blood samples from animals. The method includes detecting degradation products of NT-proBNP by various methods, including using antibodies, kits and device.

15 Claims, 8 Drawing Sheets

(56) References Cited

OTHER PUBLICATIONS

Jortani et al., "Strategies for developing biomarkers of heart failure"; Clin. Chem.; 50: 265-78 (2003).

Liu et al., "Cloning and characterization of feline brain natriuretic peptide"; Gene; 292: 183-90 (2002).

Luchner et al., "Differential expression of cardiac ANP of BNP in a rabbit model of progressive left ventricular dysfunction"; Cardiovasc. Res.; 51: 601-7 (2001).

MacDonald et al., "Brain natriuretic peptide concentration in dogs with heart disease and congestive heart failure"; J. Vet. Intern. Med.; 17(2): 172-7 (2003).

Oyama, et al., "Assessment of serum N-terminal pro-B-type natriuretic peptide concentration for differentiation of congestive heart failure from primary respiratory tract disease as the cause of respiratory signs in dogs"; J. Am. Vet. Med. Assoc.; 235:1319-25 (2009).

Seidler et al., "The amino terminal regions of proBNP and proANP oligomerise through leucine zipper-like coiled coil motifs"; Biochemical and Biophysical Research Communications; 235: 495-501 (1999).

Thomas et al., "Haemodynamic action of B-type natriuretic peptide substantially outlasts its plasma half life in conscious dogs"; Clin. Exp. Pharmacol. Physiol.; 30: 369-75 (2003).

Collins, et al., "Effects of sample handling on serum n-terminal proB-type natriutertic peptide concentration in normal dogs and dogs with heart disease", Journal of Veterinary Cardiology, 12:41-48 (2010).

Tamm, et al., "Novel Immunoassay for Quantification of Brain Natriuretic Peptide and Its Precursor in Human Blood", Clinical Chemistry, 54:1511-1518 (2008).

Lowbeer, et al., "Stability of Immulite 2000 plasma NT-proBNP in tubes with separator gel stored at room temperature", Clinica Chimica Acta, 377:283-284 (2006).

Chien, et al., "Comparison of Abbott AxSYM and Roche Elecsys 2010 for measurement of BNP and NT-proBNP", Clinica Chmica Acta, 369:95-99 (2006).

Vittorini, et al., "Cardiac natriuretic hormones: methodological aspects", Immuno Analyse Et Biologie Specialise, 22:236-246 (2007).

International Search Report mailed on Dec. 1, 2011, in International application No. PCT/US2011/046605.

Ala-Kopsala, et al., "Molecular heterogeneity has a major impact on the measurement of circulating N-terminal fragments of A- and B-type Natriurectic Peptides", Clinical Chemistry; 50:1576-1588 (2004).

Pemberton, et al., "Deconvolution Analysis of Cardiac Natriuretic Peptides During Acute Volume Overload", Hypertension; 36:355-359 (2000).

Fox, et al., "Utility of plasma N-terminal probrain natriuretic peptide (NT-proBNP) to distinguish between congestive heart failure and non-cardiac causes of acute dyspnea in cats"; Journal of Veterinary Cardiology; 11:S51-S61 (2009).

Wess, et al., "Utility of measuring plasma N-terminal pro-brain natriuretic peptide in detecting hypertrophic cardiomyopathy and differentiating grades in severity in cats"; Veterinary Clinical Pathology; 40:237-244 (2011).

Boswood, et al., "The diagnostic accuracy of different natriuretic peptides in the investigation of canine cardiac disease"; The Journal of Small Animal Practice; 1-7 (2007).

Katrukha, et al., "NT-proBNP stability assessed by several sandwich immunoassays utilizing monoclonal antibodies with different epitope specificity", AACC Annual Meeting, Jul. 24-26, 2005, Orlando, FL Poster A-83.

* cited by examiner

FIGURE 1

```
Canine preproBNP    1 MEPCAALPRALLLLLFLHLSPLGGRPHPLGGRSPAS--EASEASEASGLWAVQELLGRLK 58
Feline preproBNP    1 MDPKTALLRALLLLLFLHLSPLGGRSHPLGGPPAS--EAS--------AIQELLDGLR 49
Human  preproBNP    1 MDPQTAPSRALLLLFLHLAFLGGRSHPLGSPGSASDLETS--------GLQEQRNHLQ 51
                      *  *  * *******:****  ****  .. *** . :     . ** . *:

Canine             59 DAVSELQAEQLALEPLHRSHSPAEAPEAGGTPR-GVLAPHDSVLQALRRLRSPKMMHKSG 117
Feline             50 DTVSELQEAQMALGPLQQGHSPAESWEAQEEPPARVLAPHDNVLRALRRLGSSKMMRDSR 109
Human              52 GKLSELQVEQTSLEPLQESPRPTGVWKSREVATEGIRGHRKMVLYTLRAPRSPKMVQGSG 111
                       . **** *  :* **: .    .      .    :     :       **.:: *

Canine            118 CFGRRLDRIGSLSGLGCNVLRKY 140 [SwissProt P16859; SEQ ID NO: 1]
Feline            110 CFGRRLDRIGSLSGLGCNVLRRH 132 [SwissProt Q9GLK4; SEQ ID NO: 2]
Human             112 CFGRKMDRISSSSGLGCKVLRRH 134 [SwissProt P16860; SEQ ID NO: 3]
                      ****. ***.** *****:***:
```

The underlined portion of each sequence represents the BNP region.

KEY
* -- residues or peptides are identical in all sequences
: -- conserved substitutions are observed
. -- semi-conserved substitutions are observed

DETECTION OF DEGRADATION PRODUCTS OF CANINE NT-PROBNP

CROSS REFERENCE TO RELATED APPLICATION

This application claims benefit of U.S. Provisional Application Ser. No. 61/370,712 filed Aug. 4, 2010, which is incorporated herein by reference in its entirety.

SEQUENCE LISTING STATEMENT

The sequence listing is filed in this application in electronic format only and is incorporated by reference herein. The sequence listing text file "09-1182-US_SEQ.txt" was created on Aug. 3, 2011, and is 13,087 bytes in size.

BACKGROUND OF THE INVENTION

1. Field of the Invention

The invention is related to the detection of NT-proBNP in biological samples from canines.

2. Description of Related Art

Heart diseases affect all non-human animals. Heart diseases generally involve the cardiac valves and the cardiac muscle. Because the heart is capable of compensating for functional impairment by working harder, heart diseases in most cases remain hidden, with the consequence that the health of the heart will deteriorate due to the increased workload on the heart. The symptoms resulting from heart diseases, such as fatigue, circulatory insufficiency, and languor, can usually be recognized when the animal's heart is no longer able to compensate for the a particular functional impairment. At this stage, the heart disease has progressed to the point that curing the disease is no longer possible.

While chronic cardiac valve and cardiac muscle changes are usually incurable, the use of medicaments can slow disease progression. Therefore, an early diagnosis for heart diseases is beneficial. Routinely, physical methods are used for this purpose, such as auscultation of the heart sounds, the recording of an electrocardiogram, and X-ray and ultrasonic examinations. These examination methods have the disadvantage that they are carried out only when already visible or audible defects of the heart are recognized. Furthermore, physical examination methods require suitable and generally expensive devices in order to carry out a respective diagnosis.

In many heart diseases, such as, e.g., heart decompensation and dilated cardiomyopathy, a peptide hormone—the so-called brain natriuretic peptide (BNP)—is secreted by heart muscle tissue. Since this hormone is produced in the heart and is increasingly produced in case of overstress and congestion, determining the BNP level in blood is a suitable means for evaluating cardiac insufficiency.

BNP as well as other natriuretic peptides play an important part in regulating water balance and blood pressure. If the cardiac wall is dilated, it secrets BNP in increasing amounts, which in turn causes an excretion of sodium and liquid via the kidneys and dilation of the blood vessels. These factors can lower the blood pressure and the filling level of the heart. BNP is synthesized by the cells of the cardiac muscle as proBNP, which is cleaved into N-terminal proBNP (NT-proBNP) and BNP. Both parts of the polypeptide are delivered to the blood and can be detected therein.

The utility of both BNP and NT-proBNP as makers for cardiac disease in veterinary patients (e.g., dogs and cats) has been demonstrated in numerous studies. For instance, BNP and NT-proBNP assays have been shown to be effective as a diagnostic test for dogs, as illustrated by two studies, which report remarkably similar sensitivity and specificity (85% and 82% respectively) for differentiating the cause of clinical signs that may be attributable to cardiac disease in dogs. See Oyama M A, et al., "Assessment of serum N-terminal pro-B-type natriuretic peptide concentration for differentiation of congestive heart failure from primary respiratory tract disease as the cause of respiratory signs in dogs", Journal of American Veterinary Medical Association (December 2009); Boswood et al., "The diagnostic accuracy of different natriuretic peptides in the investigation of canine cardiac disease", JSAP 2007 1-7. In cats, the clinical challenge is different, as the most common cardiac disease in cats is hypertrophic cardiomyopathy. This disease remains occult or 'silent' with very few clinical signs that are appreciable to the pet owner until the disease is very advanced.

A number of immunoassays for the detection of NT-proBNP are known. These assays use polyclonal or monoclonal antibodies specific for epitopes within various regions of the peptide. These methods, however, are subject to variability because NT-proBNP is further processed ex vivo by various proteases in the blood serum and plasma. Therefore, immunoassays for NT-proBNP are inherently vulnerable to inconsistency due to the ex vivo degradation of the protein over time. Therefore, samples to be tested for NT-proBNP are typically refrigerated and efforts are made to conduct sample analysis as quickly as possible following taking of the sample.

Accordingly, the inventors have identified a need in the art for a method of determining NT-proBNP that can measure NT-proBNP without regard to when a sample was taken and without cumbersome handling requirements for the sample.

SUMMARY OF THE INVENTION

In one aspect, the invention is directed to a method for determining the amount of NT-proBNP in a sample from a canine, comprising determining the amount of a polypeptide selected from a sequence consisting essentially of one of GRSPASEASEASEASGLWAVQ (SED ID NO: 22) and SHSPAEAPEAGGTPRGVLAPHDSVLQ (SEQ ID NO: 30) in the sample, and correlating the amount of the polypeptide in the sample to the amount of NT-proBNP in the sample.

In another aspect, the invention is directed to a method for determining the amount of NT-proBNP in a sample from a canine, the method comprising contacting the sample with a first monoclonal antibody that specifically binds a polypeptide selected from a sequence consisting essentially of one of SEQ ID NO: 22 and SEQ ID NO: 30 or both; determining the amount of binding of at least a fragment of the NT-proBNP in the sample to the first monoclonal antibody; and associating the amount of binding to the amount of NT-proBNP in the sample.

In a further aspect, the invention is directed to a method for determining the presence or amount of NT-proBNP in a biological sample comprising forming a mixture of the sample with a first monoclonal antibody that specifically binds a fragment of NT-proBNP that is stable in the sample for at least 96 hours; allowing at least a fragment of the NT-proBNP in the sample and the monoclonal antibody to form a complex; simultaneously or sequentially contacting the mixture with a second monoclonal antibody that binds to NT-proBNP, wherein the first monoclonal antibody is immobilized on a solid phase and the second monoclonal antibody is conjugated to a label, or the first antibody is conjugated to a label and the second antibody is immobilized on the solid phase; and detecting the presence or amount of the label on the solid phase.

In yet another aspect, the invention is directed to a method for determining the presence or amount of NT-proBNP in a biological sample comprising detecting a degradation product of NT-proBNP in the sample, wherein the degradation product is a fragment of NT-proBNP that is stable in the sample for at least 96 hours.

In another aspect, the invention is directed to a kit for determining the presence, absence or level of canine NT-proBNP in a sample comprising a solid support; a first antibody, the first antibody being specific for a first epitope on a fragment of canine NT-proBNP, wherein the fragment is less than the full length of canine NT-proBNP and is stable in canine serum at room temperature for at least 96 hours after obtaining the sample; and a second antibody being specific for a second epitope on the fragment, wherein the second epitope is different than the first epitope.

In another aspect, the invention is directed to an immunoassay device comprising a solid support having a first antibody bound thereto, the first antibody being specific for a first epitope on a fragment of canine NT-proBNP; stability in canine serum at room temperature for at least 96 hours after obtaining the sample from the canine; and a second antibody being specific for a second epitope on the fragment of canine NT-proBNP, the second epitope being different than the first epitope.

BRIEF DESCRIPTION OF THE FIGURES

FIG. 1 provides an alignment of BNP polypeptide sequences from human, canine and feline (SEQ ID NOS 1-3).

DETAILED DESCRIPTION

Figure 2:
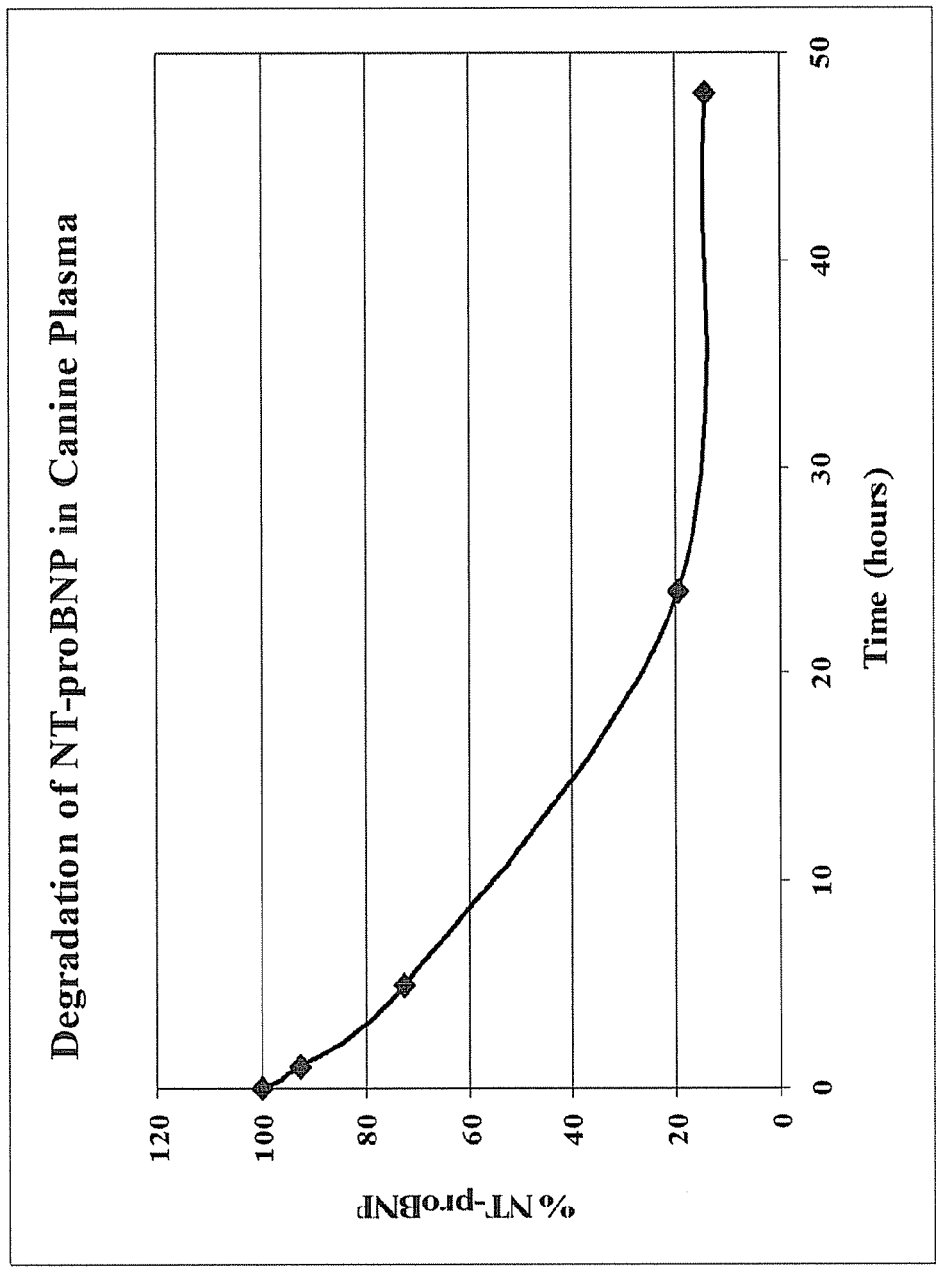
FIG. 2 shows the results of the degradation of NT-proBNP in plasma.
Figure 3:
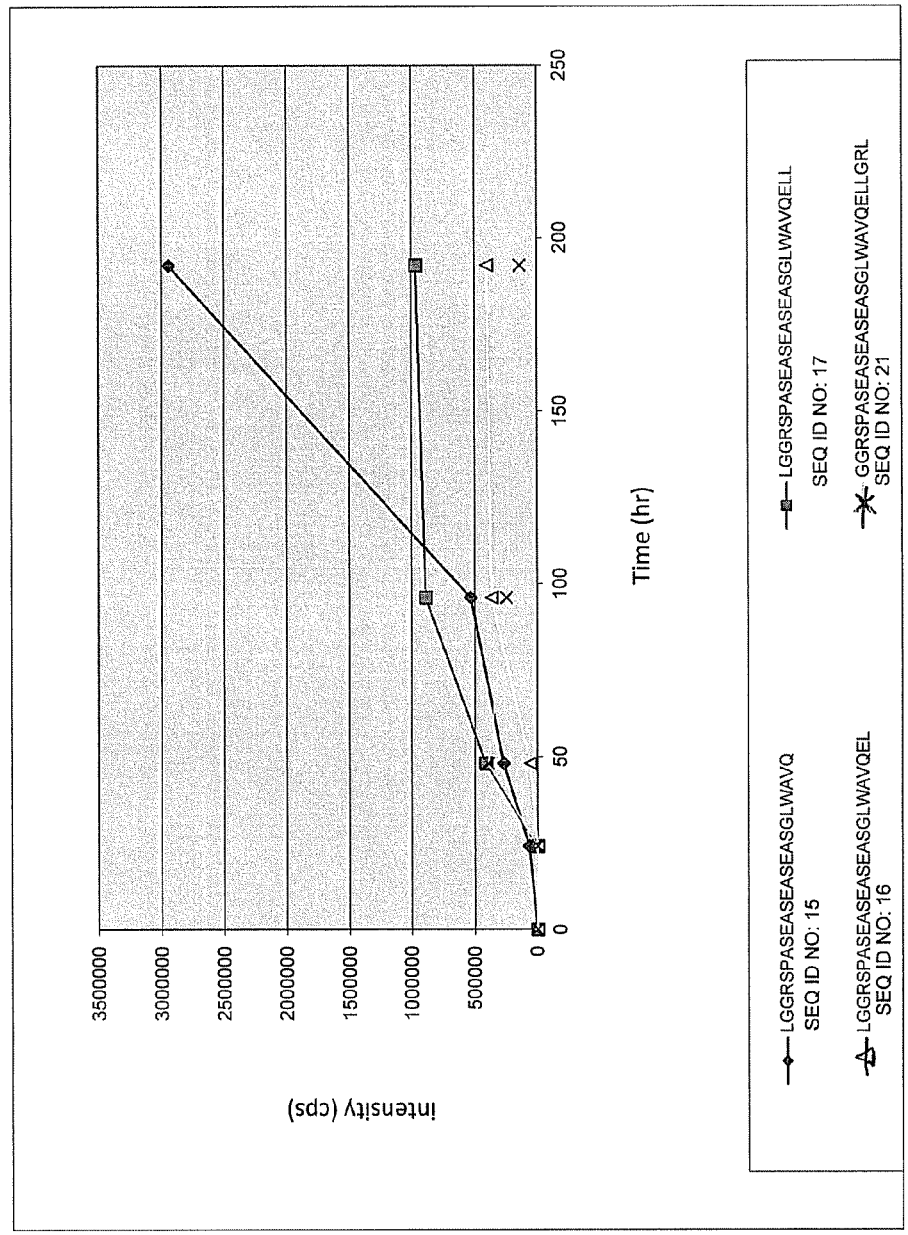
FIGS. 3-6 show the relative amounts of NT-proBNP polypeptide fragments in plasma samples after 0, 24, 96 and 192 hours of spiking with recombinant NT-proBNP.
Figure 4:
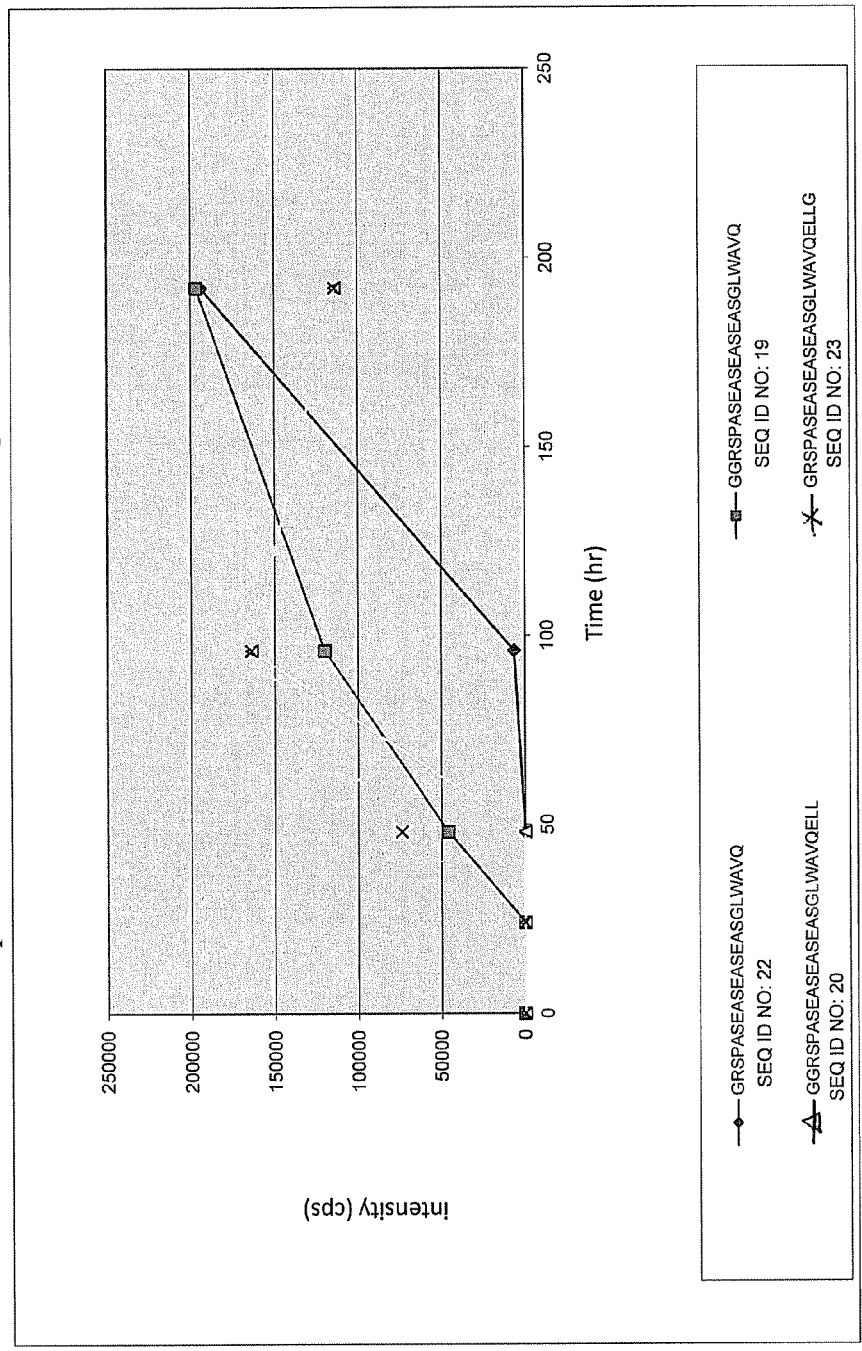
Figure 5:
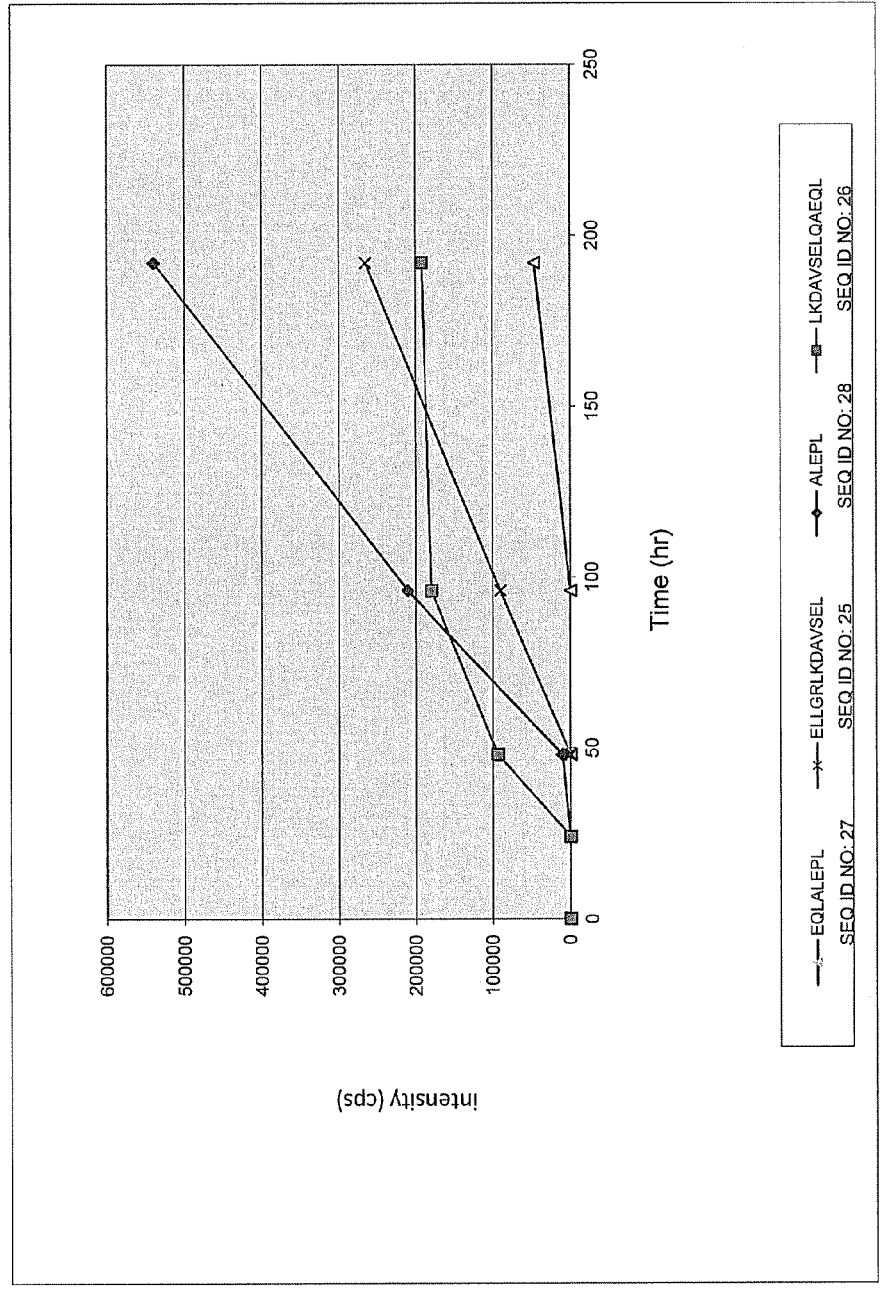
Figure 6:
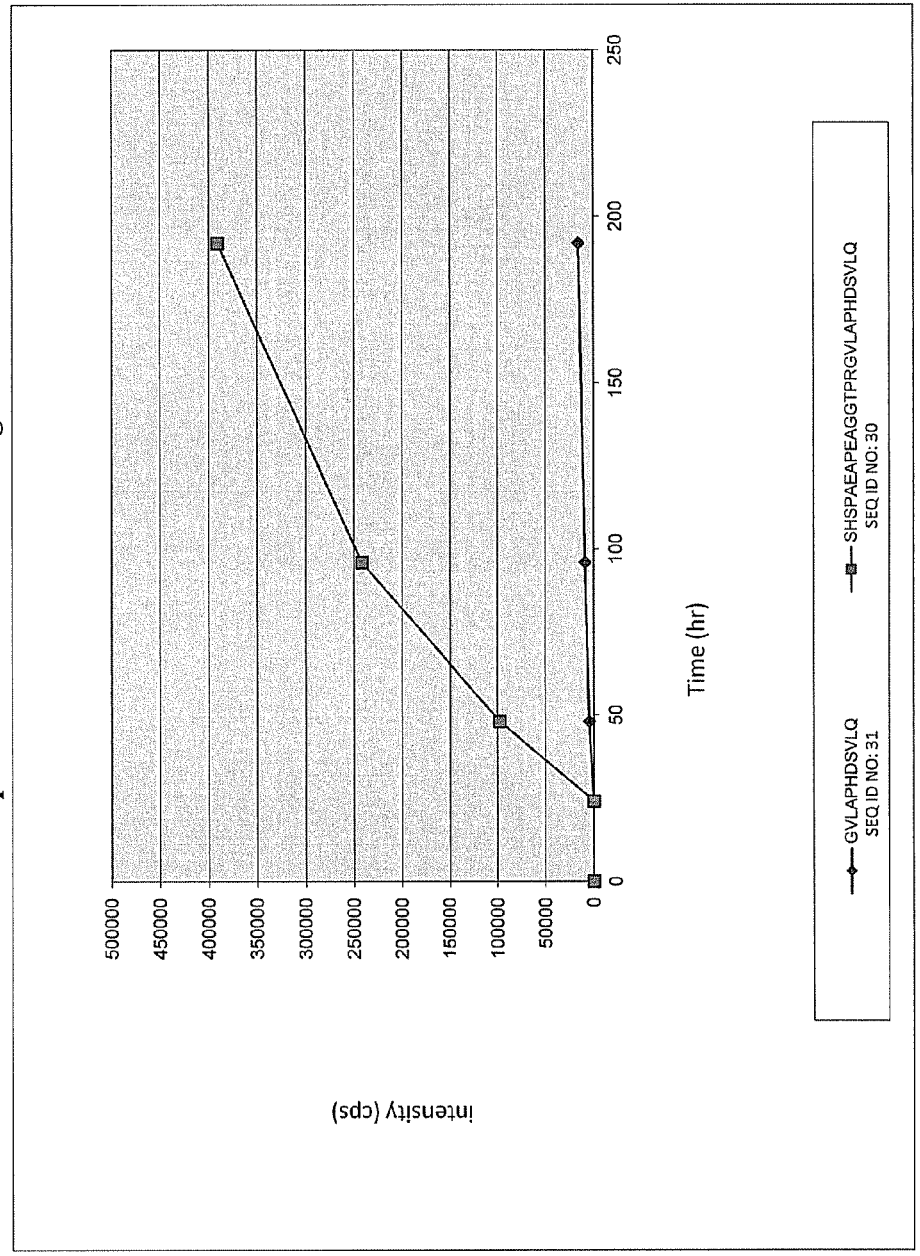

Degradation products of NT-proBNP can be determined to provide an accurate and reliable measurement of the original amount of NT-proBNP in a fresh blood sample. Because the stable degradation products, and not the NT-proBNP itself, are determined, the urgency to test the sample immediately or to refrigerate the sample prior to testing is eliminated.

There are several ways to assay a sample (e.g. whole blood, serum or plasma) for NT-proBNP or its degradation products. Mass Spectrometry, for example, can be used to look for a particular peptide sequence (e.g. full length NT-proBNP or a portion thereof). Immunoassay techniques can also be used to directly or indirectly detect full length NT-proBNP or a portion thereof. In a direct assay format, monoclonal antibodies, polyclonal antibodies or combinations thereof can be used to capture and detect full length or fragments of NT-proBNP (a.k.a. "sandwich" assays where one antibody captures the target analyte and a second, labeled antibody detects the captured analyte).

When assaying for NT-proBNP fragments in a sandwich assay, it is important to ensure the antibody pair is specific for epitopes that exist on the target, i.e. the assay will miss the fragment if one or more of the epitopes are cleaved from the original peptide or otherwise become compromised or inactivated. For example, assume the line, below, is full length canine |NT-proBNP|, wherein, over time, the peptide degrades into portions {A}, [B] and <C>, ([B] and <C> being degradation products of A):

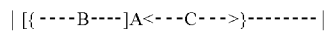

An antibody pair, one directed to an epitope on [B] and the other to an epitope on <C>, will work in a sandwich assay for {A} (or the full length peptide) as long as {A} does not split into [B] and <C>. If {A} splits into [B] and <C> a working assay for this section of the full peptide would need to have an antibody pair directed towards active epitopes on either [B] or <C>.

Alternatively, in a competition immunoassay format, only one epitope of a target fragment need be identified and targeted with either a monoclonal or polyclonal antibody. In this format, if the fragment/epitope is present, it will bind with the antibody and "compete" with a detection reagent that would have otherwise bound to the antibody.

Preferred target NT-proBNP fragments (discussed in detail, below) are those that exist in detectable concentrations over time. By determining those fragments that are stable over time one can choose Mass Spectrometry parameters or antibodies to detect and determine the concentration of the stable fragment. Once one determines the concentration of a stable fragment, the original amount of NT-proBNP in the sample can be determined.

Stable fragments NT-proBNP can also be used to purify polyclonal antibodies from sera (e.g., from chickens, goats, sheep and/or donkeys that have been immunized with all or a portion of the NT-proBNP sequence).

In order to assess the extent of heart damage or disease, determination of the quantity of NT-proBNP in a sample is helpful. Quantitative determination of the degradation products of NT-proBNP can be accomplished by several methods. Once the amount of NT-proBNP or one or more of its degradation products (the analyte) in a sample is determined, the amount NT-proBNP in the sample, prior to degradation, can be determined.

Accordingly, in one aspect the invention is directed to determining the amount of NT-proBNP in a sample from a canine, wherein the method includes determining the amount of a degradation product of NT-proBNP (i.e., a polypeptide fragment of native canine NT-proBNP). The amount of NT-proBNP in the sample can be used as a measurement of cardiac disease in the animal.

Substantial homology between species exists for BNP and NT-proBNP. For example, FIG. 1 provides an alignment of BNP polypeptide sequences from human, canine and feline (SEQ ID NOs. 1-3). As described above, BNP is processed prior to secretion from muscle cells as the N-terminal pro-BNP (NT-proBNP) and BNP.

Recombinant Canine NT-proBNP (a.k.a. rNT-proBNP or synthetic NT-proBNP) has been reported to have the following polypeptide sequence (SEQ ID NO: 4):

```
HPLGGRSPAS EASEASEASG LWAVQELLGR LKDAVSELQA
EQLALEPLHR SHSPAEAPEA GGTPRGVLAP HDSVLQALR
```

It is noted that all experiments performed herein were carried out using recombinant Canine NT-proBNP.

This peptide lacks the three C-terminal amino acids of the native sequence as a result of the expression vector used.

As shown in FIG. 2, canine NT-proBNP is degraded (cleaved in at least one location) nearly 80% after 24 hours ex vivo in plasma. Because the peptide is quickly degraded, epitopes specific for various antibodies may no longer be available for binding to the antibodies. In addition, when an assay relies upon antibody pairs that bind to the same polypeptide, cleavage through degradation of the polypeptide in the region between the two epitopes recognized by the antibodies results in the antibodies not longer being able to associate and provide a signal that is indicative of the association.

The degradation products of NT-proBNP are numerous. While all of the serum degradation products have yet to be identified, expected degradation products from a number of known proteases can be determined. For example, Table 1 shows a the expected fragments from the digestion of canine NT-proBNP with Trypsin as predicted by the Peptide Cutter application available at the ExPASy (Expert Protein Analysis System) proteomics server of the Swiss Institute of Bioinformatics (SIB).

TABLE 1

| Position of cleavage site | Resulting peptide sequence (see explanations) | Peptide length [aa] | Peptide mass [Da] | Cleavage probability |
|---|---|---|---|---|
| 6 | HPLGGR (SEQ ID NO: 5) | 6 | 635.724 | 100% |
| 30 | SPASEASEASEASGLWAVQELLGR (SEQ ID NO: 6) | 24 | 2445.625 | 100% |
| 32 | LK | 2 | 259.349 | 86.4% |
| 50 | DAVSELQAEQLALEPLHR (SEQ ID NO: 7) | 18 | 2019.242 | 100% |
| 65 | SHSPAEAPEAGGTPR (SEQ ID NO: 8) | 15 | 1463.527 | 100% |
| 79 | GVLAPHDSVLQALR (SEQ ID NO: 9) | 14 | 1475.711 | — |

As another example, Table 2 shows the expected fragments from digestion of canine NT-proBNP Proteinase K as predicted by the ExPASy Peptide Cutter application.

TABLE 2

| Position of cleavage site | Resulting peptide sequence | Peptide length [aa] | Peptide mass [Da] |
|---|---|---|---|
| 3 | HPL | 3 | 365.432 |
| 9 | GGRSPA (SEQ ID NO: 10) | 6 | 543.580 |
| 12 | SEA | 3 | 305.288 |
| 15 | SEA | 3 | 305.288 |
| 18 | SEA | 3 | 305.288 |
| 21 | SGL | 3 | 275.305 |
| 22 | W | 1 | 204.228 |
| 23 | A | 1 | 89.094 |
| 24 | V | 1 | 117.148 |
| 27 | QEL | 3 | 388.421 |
| 28 | L | 1 | 131.175 |
| 31 | GRL | 3 | 344.414 |
| 34 | KDA | 3 | 332.357 |
| 35 | V | 1 | 117.148 |
| 38 | SEL | 3 | 347.368 |
| 40 | QA | 2 | 217.225 |
| 43 | EQL | 3 | 388.421 |
| 44 | A | 1 | 89.094 |
| 45 | L | 1 | 131.175 |
| 48 | EPL | 3 | 357.407 |
| 55 | HRSHSPA (SEQ ID NO: 11) | 7 | 790.837 |
| 57 | EA | 2 | 218.210 |
| 60 | PEA | 3 | 315.326 |
| 63 | GGT | 3 | 233.224 |
| 67 | PRGV (SEQ ID NO: 12) | 4 | 427.504 |
| 68 | L | 1 | 131.175 |

TABLE 2-continued

| Position of cleavage site | Resulting peptide sequence | Peptide length [aa] | Peptide mass [Da] |
|---|---|---|---|
| 69 | A | 1 | 89.094 |
| 74 | PHDSV (SEQ ID NO: 13) | 5 | 553.572 |
| 75 | L | 1 | 131.175 |
| 77 | QA | 2 | 217.225 |
| 78 | L | 1 | 131.175 |
| 79 | R | 1 | 174.203 |

For nomenclature purposes, the canine NT-proBNP sequence can be loosely divided into three regions: N-terminal region (usually including amino acids 1-22); middle region (usually including amino acids 23-50), and C-Terminal region (usually including amino acids 51-79). Polypeptide sequence fragments from these regions were noted at 24 or 196 hours as shown below.

N-terminal region (24 hours):

LGGRSPASEASEASEASGLWAVQELLGR (SEQ ID NO: 14)

N-terminal region (192 hours)

LGGRSPASEASEASEASGLWAVQ (SEQ ID NO: 15)

LGGRSPASEASEASEASGLWAVQEL (SEQ ID NO: 16)

LGGRSPASEASEASEASGLWAVQELL (SEQ ID NO: 17)

LGGRSPASEASEASEASGLWAVQELLGR (SEQ ID NO: 14)

GGRSPASEASEASEASGLWAVQ (SEQ ID NO: 19)

GGRSPASEASEASEASGLWAVQELL (SEQ ID NO: 20)

GGRSPASEASEASEASGLWAVQELLGRL (SEQ ID NO: 21)

GRSPASEASEASEASGLWAVQ (SEQ ID NO: 22)

GRSPASEASEASEASGLWAVQELLG (SEQ ID NO: 23)

In the above sequences, the N-terminal -HP- from the native sequence is cleaved in all cases, -L- and then the first -G- are also cleaved over time. Antibodies raised against peptides having the N-terminal -HP-, -HPL- and/or -HPLG- have been shown to have decreased sensitivity as samples age.

Middle region (192 hours)

LWAVQELLGRLKDAVSELQAEQLALEPLHRSHSPAEAPEAGGTPRGVL (SEQ ID NO: 24)

ELLGRLKDAVSEL (SEQ ID NO: 25)

LKDAVSELQAEQL (SEQ ID NO: 26)

EQLALEPL (SEQ ID NO: 27)

ALEPL (SEQ ID NO: 28)

C-terminal region (192 hours)

SHSPAEAPEAGGTPRGVLAPHDSVLQ (SEQ ID NO: 30)

GVLAPHDSVLQ (SEQ ID NO: 31)

FIGS. 3-6 show the relative amount of these fragments in the plasma samples at 0, 24, 96 and 192 hours. The most prevalent polypeptides after 192 hours were GRS-PASEASEASEASGLWAVQ (SEQ ID NO: 22) in the N-terminal region and SHSPAEAPEAGGTPRGVLAPHDSVLQ (SEQ ID NO: 30) in the C-terminal region.

The invention also provides antibodies that selectively bind to one of the NT-proBNP degradation products, as well as variants and further fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. In one aspect, the antibodies of the invention are monoclonal antibodies produced by a mouse myeloma cell line. This cell line can be made by fusing a mouse myeloma cell line with the spleen cells from mice that have been injected with the NT-proBNP fragments described herein and suitable carrier proteins that are well known to those of skill in the art.

In a preferred method of making monoclonal antibodies of the present invention, the selected immunogen is a combination of the two peptides conjugated from both the N-terminus and the C-terminus. For example, with respect to two of the most preferred stable peptides: N-terminal GRS-PASEASEASEASGLWAVQ (SEQ ID NO: 22) and C-terminal SHSPAEAPEAGGTPRGVLAPHDSVLQ (SEQ ID NO: 30); the N-terminal immunogen is a combination of GRS-PASEASEASEASGLWAVQ-(PEG)6-Cys-KLH (SEQ ID NO: 32) and KLH-Cys-(PEG)6-GRSPASEASEASEASGL-WAVQ (SEQ ID NO: 33), while the C-terminal immunogen is a combination of SHSPAEAPEAGGTPRGVLAPHDS-VLQ-(PEG)6-Cys-KLH (SEQ ID NO: 34) and KLH-Cys-(PEG)6-SHSPAEAPEAGGTPRGVLAPHDSVLQ (SEQ ID NO: 35). Using standard techniques, the aforementioned immunogens were used to obtain murine antibodies that were able to detect stable canine NT-proBNP fragements in blood samples.

The antibodies can be used to isolate NT-proBNP or a fragment thereof by standard techniques, such as affinity chromatography or immunoprecipitation. In one aspect, the invention is directed to an immunological method for detecting the presence of an amount of NT-proBNP in a biological sample. The invention provides a method, a device and a kit that uses one or more canine NT-proBNP monoclonal antibodies. In another aspect, the method includes calibrators and standards comprising one or more NT-proBNP polypeptides.

"Binding specificity" or "specific binding" refers to the substantial recognition of a first molecule for a second molecule, for example a polypeptide and a polyclonal or monoclonal antibody, or an antibody fragment (e.g., a Fv, single chain Fv, Fab', or F(ab')$_2$ fragment) specific for the polypeptide.

A "specific binding pair" is a set of two different molecules, where one molecule has an area on its surface or in a cavity that specifically binds to, and is therefore complementary to, an area on the other molecule. "Specific binding partner" refers to one of these two complementarily binding molecules. "Specific binding pair" may refer to a ligand and a receptor, for example. In another example, the specific binding pair might refer to an immunological pair, for example an antigen and antibody.

"Substantial binding" or "substantially bind" refer to an amount of specific binding or recognizing between molecules in an assay mixture under particular assay conditions. In its broadest aspect, substantial binding relates to the difference between a first molecule's inability to bind or recognize a second molecule, and the first molecules ability to bind or recognize a third molecule, such that the difference is sufficient to allow a meaningful assay to be conducted distinguishing specific binding under a particular set of assay conditions, which includes the relative concentrations of the molecules, and the time and temperature of an incubation. In another aspect, one molecule is substantially incapable of binding or recognizing another molecule in a cross-reactivity sense where the first molecule exhibits reactivity for a second molecule that is less than 25%, preferably less than 10%, more preferably less than 5% of the reactivity exhibited toward a third molecule under a particular set of assay conditions, which includes the relative concentration and incubation of the molecules. Specific binding can be tested using a number of widely known methods, e.g, an immunohistochemical assay, an enzyme-linked immunosorbent assay (ELISA), a radioimmunoassay (RIA), or a western blot assay.

A "blood sample" refers to a whole blood sample from an animal or its components (e.g., serum, plasma, etc.).

A "label" is any molecule that is bound (via covalent or non-covalent means, alone or encapsulated) to another molecule or solid support and that is chosen for specific characteristics that allow detection of the labeled molecule. Generally, labels are comprised of, but are not limited to, the following types: particulate metal and metal-derivatives, radioisotopes, catalytic or enzyme-based reactants, chromogenic substrates and chromophores, fluorescent and chemiluminescent molecules, and phosphors. The utilization of a label produces a signal that may be detected by means such as detection of electromagnetic radiation or direct visualization, and that can optionally be measured.

The label employed in the current invention could be, but is not limited to: alkaline phosphatase; glucose-6-phosphate dehydrogenase ("G6PDH"); horse radish peroxidase (HRP); chemiluminescers such as isoluminol, fluorescers such as fluorescein and rhodamine compounds; ribozymes; and dyes.

The label can directly produce a signal, and therefore additional components are not required to produce a signal. Alternatively, a label may need additional components, such as substrates or co-enzymes, in order to produce a signal. The suitability and use of such labels useful for producing a signal are discussed in U.S. Pat. No. 6,489,309, and U.S. Pat. No. 5,185,243, which are incorporated by reference herein in their entirety. For example, a label may be conjugated to the specific binding partner in a non-covalent fashion. Alternatively, the label may be conjugated to the specific binding partner covalently. U.S. Pat. No. 3,817,837, and U.S. Pat. No. 3,996,345, which are incorporated by reference herein in their entirety, describe in detail example of various ways that a label may be non-covalently or covalently conjugated to the specific binding partner.

"Solid phase" means a porous or non-porous water insoluble material. Such materials include a support or a surface such as the wall of a reaction vessel. The support can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystyrene, polymethacrylate, poly(ethylene terephthalate), nylon, poly(vinyl butyrate), etc.; either used by themselves or in conjunction with other materials; glass available as Bioglass, ceramics, metals, and the like. Natural or synthetic assemblies such as liposomes, phospholipid vesicles, and cells can also be employed.

Binding of specific binding pair members to a support or surface may be accomplished by well-known techniques, commonly available in the literature. See, for example "Immobilized Enzymes," Ichiro Chibata, Halsted Press, New York (1978) and Cuatrecasas, *J. Biol. Chem.*, 245:3059 (1970). The surface can have any one of a number of shapes, such as strip, rod, particle, including bead, and the like. In one aspect, the polypeptides of the invention include a N-terminal cysteine residue to assist in binding the polypeptides to the solid phase.

The method of the invention can be optimized in many ways and one of skill in the art could simultaneously adjust the sample dilutions, reagent concentrations, incubation temperatures and times used in the method to accomplish detection of NT-proBNP.

To be useful in the detection methods of the present invention, the polypeptides are obtained in a substantially pure form, that is, typically from about 50% w/w or more purity, substantially free of interfering proteins and contaminants. Preferably, the polypeptides are isolated or synthesized in a purity of at least 80% w/w, and more preferably, in at least about 95% w/w purity. Using conventional protein purification techniques, homogeneous polypeptide compositions of at least about 99% w/w purity can be obtained. For example, the proteins may be purified by use of the antibodies described hereinafter using the immunoabsorbant affinity columns described hereinabove.

The method of the invention may be accomplished using immunoassay techniques well known to those of skill in the art, including, but not limited to, using microplates and lateral flow devices. In one embodiment, an antibody specific for NT-proBNP protein is immobilized on a solid support at a distinct location. Following addition of the sample, detection of protein-antibody complexes on the solid support can be by any means known in the art. For example, U.S. Pat. No. 5,726,010, which is incorporated herein by reference in its entirety, describes an example of a lateral flow device, the SNAP® immunoassay device (IDEXX Laboratories), useful in the present invention. In another aspect, the solid support is a well of a microtiter plate.

Immobilization of one or more analyte capture reagents, e.g., antibodies to NT-proBNP, onto a device or solid support is performed so that an analyte capture reagent will not be washed away by the sample, diluent and/or wash procedures. One or more analyte capture reagents can be attached to a surface by physical adsorption (i.e., without the use of chemical linkers) or by chemical binding (i.e., with the use of chemical linkers). Chemical binding can generate stronger attachment of specific binding substances on a surface and provide defined orientation and conformation of the surface-bound molecules.

In another aspect, the invention includes one or more labeled specific binding reagents that can be mixed with a test sample prior to application to a device for of the invention. In this case it is not necessary to have labeled specific binding reagents deposited and dried on a specific binding reagent pad in the device. A labeled specific binding reagent, whether added to a test sample or pre-deposited on the device, can be for example, a labeled NT-proBNP monoclonal antibody.

The detection method may include the use of a standard such as a recombinant NT-proBNP polypeptide. The standard can be mixed with the monoclonal antibody or antibodies in the same manner as the sample. The amount of binding between the monoclonal antibody or antibodies and the standard can be compared to the amount of binding of the antibodies to the protein in the sample. Accordingly, because the amount of NT-proBNP in the standard is known, the amount of protein in the sample can be determined.

Any or all of the above embodiments can be provided as a kit. In one particular example, such a kit would include a device complete with specific binding reagents (e.g., a non-immobilized labeled specific binding reagent and an immobilized analyte capture reagent) and wash reagent, as well as detector reagent and positive and negative control reagents, if desired or appropriate. In addition, other additives can be included, such as stabilizers, buffers, and the like. The relative amounts of the various reagents can be varied, to provide for concentrations in solution of the reagents that substantially optimize the sensitivity of the assay. Particularly, the reagents can be provided as dry powders, usually lyophilized, which on dissolution will provide for a reagent solution having the appropriate concentrations for combining with a sample.

The device may also include a liquid reagent that transports unbound material (e.g., unreacted fluid sample and unbound specific binding reagents) away from the reaction zone (solid phase). A liquid reagent can be a wash reagent and serve only to remove unbound material from the reaction zone, or it can include a detector reagent and serve to both remove unbound material and facilitate analyte detection. For example, in the case of a specific binding reagent conjugated to an enzyme, the detector reagent includes a substrate that produces a detectable signal upon reaction with the enzyme-antibody conjugate at the reactive zone. In the case of a labeled specific binding reagent conjugated to a radioactive, fluorescent, or light-absorbing molecule, the detector reagent acts merely as a wash solution facilitating detection of complex formation at the reactive zone by washing away unbound labeled reagent.

Two or more liquid reagents can be present in a device, for example, a device can comprise a liquid reagent that acts as a wash reagent and a liquid reagent that acts as a detector reagent and facilitates analyte detection.

A liquid reagent can further include a limited quantity of an "inhibitor", i.e., a substance that blocks the development of the detectable end product. A limited quantity is an amount of inhibitor sufficient to block end product development until most or all excess, unbound material is transported away from the second region, at which time detectable end product is produced.

Detection of NT-proBNP by Mass Spectroscopy

Peptides and peptide fragments of the invention may be detected using standard mass spectrometric techniques. In mass spectrometry (MS), the analyte is first vaporized and ionized, then the ions are directed to a mass analyzer, in which electromagnetic fields are used to separate species by mass. Lastly, a detector quantifies the abundance of each species.

Standard ionization techniques that are well known in the art include electrospray ionization (ESI) and matrix-assisted laser desorption ionization (MALDI), which are commonly used with liquid and solid biological samples. Other ionization technologies known in the art include thermal ionization (TIMS), spark ionization, secondary ion mass spectrometry (SIMS), atmospheric pressure chemical ionization (APCI), ion attachment ionization, direct analysis in real time (DART), desorption/ionization on silicon (DIOS), thermospray ionization, fast atom bombardment (FAB), field desorption, glow discharge, and inductively couple plasma (ICP). Examples of well-known mass analyzers include sector field, time-of-flight (TOF), quadrupole, quadrupole ion trap (IT), linear quadrupole ion trap, Fourier transform ion cyclotron resonance (FT-ICR), and orbitrap mass analyzers. Examples of well-known detectors include electron multiplier, Faraday cup, microchannel plate, and Daly detectors.

Mass analyzers segregate ions according to their mass-to-charge ratio (m/z, where m is mass and z is charge). For example, a peptide of molecular weight P with two positive charges will have a net mass of (P+2) due to the ionizing presence of two protons, and will appear on a mass spectrum at m/z=(P+2)/2. Thus, in general, a molecule of molecular weight M with charge Z will appear on a mass spectrum at m/z=(M+Z)/Z.

Mass spectrometry can be combined with liquid chromatography (LC) or gas chromatography (GC) to facilitate detection and identification of compounds residing within a complex mixture. In liquid chromatography-mass spectrometry (LC/MS), the analyte solution is first passed through a high-performance liquid chromatography (HPLC) column, which may separate components by a characteristic such as hydrophobicity, partition coefficient, polarity, bioaffinity, charge, or size using well-known chromatographic techniques such as reversed-phase chromatography, normal phase chromatography, displacement chromatography, partition chromatography, ion exchange chromatography, size exclusion chromatography, or bioaffinity chromatography. The mass spectrometer then generates a mass spectrum for each peak in the HPLC chromatogram. Using LC/MS, a single species of interest can be separated and identified from within complex biological mixtures such as plasma or serum.

LC can also be combined with a tandem mass spectrometer (MS/MS), which is capable of multiple rounds of mass spectrometry for purposes such as protein identification. An MS/MS system can isolate and stabilize an individual ion species appearing in a mass spectrum, which is then fragmented using any one of several well-known techniques, such as collision-induced dissociation (CID), electron capture dissociation (ECD), electron transfer dissociation (ETD), infrared multiphoton dissociation (IRMPD), and blackbody infrared radiative dissociation (BIRD). The fragments are themselves analyzed by MS to generate a fragment mass spectrum, also called a fragmentation pattern. In the case of protein identification, an experimentally derived fragmentation pattern (generated from a sample with an unknown protein or peptide) can be compared with fragmentation patterns that have been predicted from information in protein sequence or nucleotide sequence databases. A high degree of similarity between experimental and predicted fragmentation patterns leads to identification of the unknown protein in the sample.

Other features and advantages of the invention will be apparent from the following Examples. The following are provided for exemplification purposes only and are not intended to limit the scope of the invention described in broad terms above. All references cited in this disclosure are incorporated herein by reference.

EXAMPLES

LC/MS analyses were obtained using a Thermo-Scientific LTQ ORBITRAP DISCOVERY™ system.

For plasma extraction, 100 uL of plasma was precipitated by addition of 200 uL methanol in a 1.5 mL protein LoBind eppendorf tube. After vortexing for 10 seconds, the precipitate was pelleted by centrifugation at 13,000 rpm for 15 minutes at 10° C. using a benchtop centrifuge. The supernatant was transferred to a limited volume glass HPLC vial and analyzed by LC/MS as described in the following examples.

Example 1

Mass Spectra of rNT-proBNP in Water, Serum Extract, and Plasma Extract.

A sample containing canine rNT-proBNP in water at a concentration of 10 µg/mL was analyzed by LC/MS. The resulting mass spectrum contains a predominant peak corresponding to the +10 charge state of the NT-proBNP peptide (m/z=821.9).

To demonstrate detection of the peptide in serum and plasma extracts, 1 µg/mL of NT-proBNP was added to water, serum extract, and plasma extract, and each sample was then analyzed by LC/MS Full Scan mode. The +10 charge state of NT-proBNP (m/z=821.9) is clearly visible in all resulting spectra.

An additional experiment was conducted to compare mass spectra of serum and plasma extracts with and without the addition of 1 µg/mL of canine rNT-proBNP. As above, each sample was analyzed by LC/MS full scan mode. Peaks corresponding to rNT-proBNP are clearly visible in samples with rNT-proBNP added, and are absent from the blank samples (without NT-proBNP added).

Example 2

MS Analysis of Degradation Kinetics of NT-proBNP in Canine Plasma

Degradation kinetics of whole rNT-proBNP in canine plasma were investigated by adding 1 µg to 1 mL of canine plasma; then, aliquots of the plasma were analyzed by LC/MS at 0, 1, 5, 24, and 48 hours after addition of the peptide. As shown in FIG. 2, approximately 80% of the peptide was degraded after 24 hours.

The LC gradient is shown in Table 3, where Solvent C is 1% acetic acid in water and Solvent D is 1% acetic acid in acetonitrile.

TABLE 3

LC gradient for analysis of degradation products.

| No | Time | A % | B % | C % | D % | µL/min |
|---|---|---|---|---|---|---|
| 1 | 0 | 0 | 0 | 95 | 5 | 500 |
| 2 | 1.5 | 0 | 0 | 95 | 5 | 500 |
| 3 | 11.5 | 0 | 0 | 5 | 95 | 500 |
| 4 | 14.5 | 0 | 0 | 5 | 95 | 500 |
| 5 | 16.0 | 0 | 0 | 95 | 5 | 500 |
| 6 | 17.5 | 0 | 0 | 95 | 5 | 500 |

Column: Acquity UPLC BEH300 C4 1.7 µM 2.1 id×50 mm length
Guard Column: vanguard BEH 300 C4 1.7 uM
Injection volume: 20 µL
Tray temp: 20° C.
Column oven temp: 30° C.
MS run time: 17.5 minutes
The divert valve parameters used for degradation product LC/MS analysis are shown in Table 4.

TABLE 4

| Divert Time | Valve State |
|---|---|
| 0.00 | To waste |
| 2.07 | To source |
| 15.57 | To waste |

MS scan event 1: FTMS; resolution 30000; scan range 700.0-1800.0
MS scan event 2: FTMS; resolution 30000; scan range 821.4-822.4
MS Tune File Values
Source Type: ESICapillary Temp (° C.): 350.00
Sheath gas Flow: 34.5
Aux Gas Flow: 2.0
Sweep Gas Flow: 0
FTMS Injection waveforms: off
FTMS AGC Target: 500000
Source voltage (kV): 4.00
Source current (µA): 100.00
Capillary Voltage (V): 39.00
Tube Lens (V): 110.00
Skimmer Offset (V): 0.00
Multipole RF Amplifier (Vp-p): 400.00
Multipole 00 offset (V): −3.75
Lens 0 Voltage (V): −3.50
Multipole 0 offset (V): −6.00
Lens 1 Voltage (V): −23.00
Gate Lens offset (V): −22.00
Multipole 1 offset (V): −6.50
Front Lens (V): −6.50
FTMS full microscans: 3
FTMS full Max Ion Time (ms): 100

Example 3

Characterization of Trypsin and Proteinase K Degradation Products by MS

To characterize the proteolytic degradation products of canine rNT-proBNP, 2 µg of proteomics grade trypsin (Sigma Aldrich, St. Louis Mo.) was added to 1 µg of NT-proBNP in 1 mL of 50 mM Tris acetate buffer, pH 8.5. The mixture was incubated at 37° C. overnight, then analyzed by LC/MS. Ethanol was injected as a blank.

LC/MS of degradation products was conducted using the following parameters.

The LC gradient is shown in Table 5, where Solvent C is 1% acetic acid in water and Solvent D is 1% acetic acid in acetonitrile.

TABLE 5

| No | Time | A % | B % | C % | D % | µL/min |
|---|---|---|---|---|---|---|
| 1 | 0 | 0 | 0 | 100 | 0 | 300 |
| 2 | 5.0 | 0 | 0 | 100 | 0 | 300 |
| 3 | 65.0 | 0 | 0 | 70 | 30 | 300 |
| 4 | 68.0 | 0 | 0 | 5 | 95 | 300 |
| 5 | 78.0 | 0 | 0 | 5 | 95 | 300 |
| 6 | 80 | 0 | 0 | 100 | 0 | 300 |
| 7 | 90 | 0 | 0 | 100 | 0 | 300 |

Column: Acquity UPLC BEH300 C4 1.7 µM 2.1 id×150 mm length
Guard Column: vanguard BEH 300 C4 1.7 uM
Injection volume: 20 µL
Tray temp: 20° C.
Column oven temp: 30° C.
MS run time: 90.0 minutes The divert valve parameters used for stable peptide LC/MS analysis are shown in Table 6.

TABLE 6

| DivertTime | Valve State |
|---|---|
| 0.00 | To waste |
| 5.05 | To source |
| 84.25 | To waste |

MS scan event 1: FTMS; resolution 30000; scan range 150.0-1500.0
MS scan event 2-6: ITMS+c norm Dep MS/MS $1^{st}, 2^{nd}, 3^{rd}, 4^{th}$, and $5^{th}$; most intense ion from respectively from scan 1.
Activation Type: CID
Min Signal Required: 1000
Isolation Width: 2.0
Normalized Coll. Energy: 35.0
Default Charge State: 2
Activation Q: 0.250
Activation Time: 30.000
CV=0.0V
Data Dependent Settings:
Use separate polarity settings disabled
Parent Mass List: none
Reject Mass List: none
Neutral loss Mass List: none
Product Mass List: none
Neutral loss in top: 3
Product in top: 3
Most intense if no parent masses found not enabled
Add/subtract mass not enabled
FT master scan preview mode enabled
Charge state screening enabled
Monoisotopic precursor selection enabled
Non-peptide monoisotopic recognition not enabled
Charge state rejection enabled
Unassigned charge states: rejected
Charge state 1: not rejected
Charge state 2: not rejected
Charge state 3: not rejected
Charge state 4+: not rejected
Global Data Dependent Settings
Use global parent and reject mass lists not enabled
Exclude parent mass from data dependent selection not enabled
Exclusion mass width relative to mass
Exclusion mass width relative to low (ppm): 20.00
Exclusion mass width relative to high (ppm): 20.00
Parent mass width by mass
Parent mass width low: 0.500000
Parent mass width high: 0.500000
Reject mass width relative to mass
Reject mass width low (ppm): 20.00
Reject mass width high (ppm): 20.00
Zoom/UltraZoom scan mass width by mass
Zoom/UltraZoom scan mass low: 5.00
Zoom/UltraZoom scan mass high: 5.00
FT SIM scan mass width low: 5.00
FT SIM scan mass width high: 5.00
Neutral Loss candidates processed by decreasing intensity
Neutral loss mass width by mass
Neutral Loss mass width low: 0.50000
Neutral Loss mass width high: 0.50000
Product candidates processed by decreasing intensity
Product mass width by mass
Product mass width low: 0.50000
Product mass width high: 0.50000
MS mass range: 0.00-1000000.00
Use m/z values as masses not enabled
Analog UV data dep. Not enabled
Dynamic exclusion enabled
Repeat Count: 1
Repeat Duration: 30.00
Exclusion List Size: 500
Exclusion Duration: 60.00
Exclusion mass width relative to mass
Exclusion mass width low (ppm): 20.00
Exclusion mass width high (ppm): 20.00
Isotopic data dependence not enabled
Mass Tags data dependence not enabled
Custom Data Dependent Settings not enabled
MS Tune File Values
Source Type: ESI
Capillary Temp (° C.): 350.00
Sheath gas Flow: 34.5
Aux Gas Flow: 2.0
Sweep Gas Flow: 0
FTMS Injection waveforms: off
FTMS AGC Target: 500000
Source voltage (kV): 4.00
Source current (µA): 100.00
Capillary Voltage (V): 33.00
Tube Lens (V): 235.00
Skimmer Offset (V): 0.00
Multipole RF Amplifier (Vp-p): 400.00
Multipole 00 offset (V): −3.25
Lens 0 Voltage (V): −4.00
Multipole 0 offset (V): −6.00
Lens 1 Voltage (V): −12.00
Gate Lens offset (V): −58.00
Multipole 1 offset (V): −6.50
Front Lens (V): −6.50
FTMS full microscans: 3
FTMS full Max Ion Time (ms): 100

The predominant Tryptic fragments observed were GVLAPHDSVLQALR (SED ID NO: 9) (mol. wt. 1475), SHSPAEAPEAGGTPR (SED ID NO: 8) (mol. wt. 1463), LKDAVSELQAEQLALEPLHR (SED ID NO: 36) (mol. wt. 2260), and SPASEASEASEASGLWAVQELLGR (SED ID NO: 6) (mol. wt. 2445), which were highly similar to the fragments predicted using Peptide Cutter application available at the ExPASy (Expert Protein Analysis System) proteomics server of the Swiss Institute of Bioinformatics (SIB) (see Table 1 for theoretical tryptic map of NT-proBNP).

A similar experiment was conducted using proteinase K instead of trypsin. 1 µg of proteomics grade proteinase K was added to 10 µg of canine rNT-proBNP in 1 mL of 50 mM Tris HCl and 10 mM $CaCl_2$, pH 8.0. The mixture was incubated at 47° C. for 3 hours, then analyzed by LC/MS. Ethanol was injected as a blank. ALEPL (SED ID NO: 28) (mol. wt. 542), HPLGGRSPASEAS (SED ID NO: 40) (mol. wt. 1265), DAVSEL (SED ID NO: 41) (mol. wt. 633), and LEPL (SED ID NO: 42) (mol. wt. 471) were among the proteinase K fragments observed in the mass spectrum. A theoretical proteinase K digestion map is shown in Table 2.

Example 4

Characterization of Stable Degradation Products of Canine NT-proBNP

To characterize the rNT-proBNP stable degradation products present after incubation in canine plasma, canine rNT-proBNP was added to canine plasma at 1, 5, and 10 µg/mL and incubated at room temperature. At 24, 48, 96, and 192 hours, 100 µL aliquots of the plasma were collected and combined with 200 µL of methanol to form a precipitate. After centrifugation, the supernatant was analyzed for stable peptides by LC/MS as described in Example 3.

After 24 hours, the fragment LGGRSPASEASEASEAS-GLWAVQELLGR (SED ID NO: 14) was observed in the sample containing 10 µg/mL NT-proBNP, indicating cleavage between the detector and capture regions of the full-length peptide.

After 192 hours, identified fragments included HSPAEA-PEAGGTPRVLAPHDSVLQ (SED ID NO: 30), GVLAPHDSVLQ (SED ID NO: 31), and LWAVQELLGR-LKDAVSELQAEQLALEPLHRSHSPAEA-PEAGGTPRGVL (SED) ID NO: 24).

The relative abundance of several fragments from the N-terminal, capture, and C-terminal regions were evaluated over time. These data are shown in FIGS. 3-6, and indicate that the most stable fragment sequences over time were GRS-PASEASEASEASGLWAVQ (SEQ ID NO: 22) from the N-terminal region and SHSPAEAPEAGGTPRGVLAPHDS-VLQ (SEQ ID NO: 30) from the C-terminal region.

Example 5

Identification of Stable Epitopes of Canine NT-proBNP

To identify stable peptide epitopes, a database containing the amino acid sequence of rNT-proBNP HPLGGRSPAS EASEASEASG LWAVQELLGR LKDAVSELQAEQLA-LEPLHR SHSPAEAPEA GGTPRGVLAP HDSVLQALR (SEQ ID NO: 4) in FASTA format was created. The .RAW file of interest acquired from the LC-MS run was uploaded along with the FASTA database to Proteome Discoverer software (v 1.0 Thermo Scientific) for identification of the stable epitopes.

The peptides that satisfy the criteria as directed in the Proteome Discover Software were indentified as stable epitopes for a particular time series.

Example 6

Immunoassay

Figure 7:
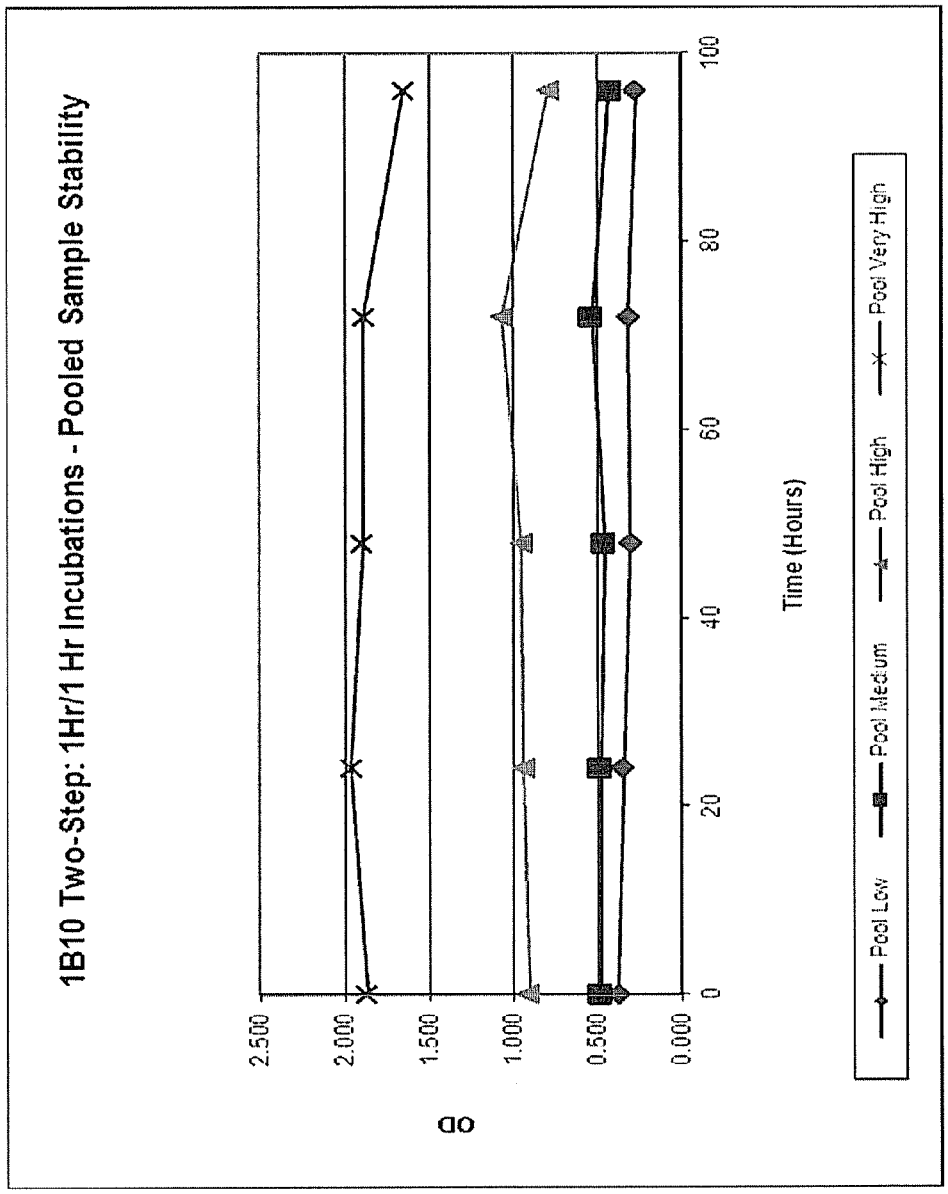
FIG. 7 shows the results of a sandwich assay using a monoclonal antibody specific for a stable fragment of NT-proBNP of the course of 96 hours.
Figure 8:
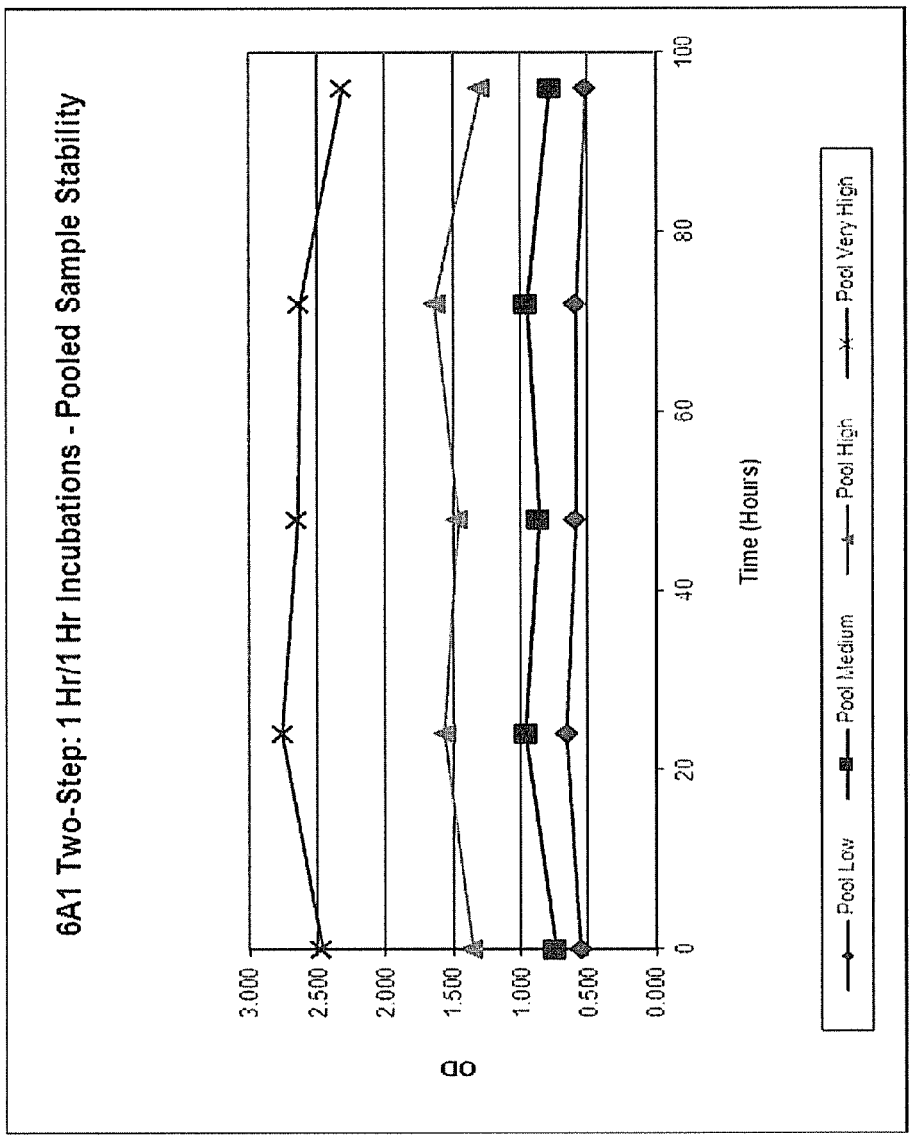
FIG. 8 shows the results of a sandwich assay using a monoclonal antibody specific for a stable fragment of NT-proBNP over the course of 96 hours.

Immunoassays were conducted using monoclonal antibodies specific for SEQ ID stable canine NT-proBNP degradation fragments (SEQ ID NOS: 22 and 30) at 24, 48, 72 and 96 hours. Sheep polyclonal antibodies raised against c-KDAVSELQAEQLALEPL (SEQ ID NO: 37) were coated on a solid phase. Detection antibodies were monoclonal antibodies raised against the SEQ ID NOS: 22 and 30 conjugated at both the N and C terminus with a protein carrier: (i) GRS-PASEASEASEASGLWAVQ-(PEG)6-Cys-KLH (SEQ ID No. 32) and KLH-Cys-(PEG) 6-GRSPASEASEASEASGL-WAVQ (SEQ ID No. 33); and/or ii) SHSPAEAPEAGGT-PRGVLAPHDSVLQ-(PEG)6-Cys-KLH (SEQ ID No. 34) and KLH-Cys(PEG)6-SHSPAEAPEAGGTPRGV-LAPHDSVLQ (SEQ ID No. 35). The monoclonal detection antibodies raised against the above immunogens were labeled with HRP using standard techniques. Canine plasma was incubated with the solid phase for 1 hour followed by a second incubation with the labeled detection antibodies. Results of the assay are shown in FIGS. 7 and 8. In this method, the assay detected longer fragments that included both SEQ ID NO: 37 and one of SEQ ID NO: 22 and 30.

The examples given above are merely illustrative and are not meant to be an exhaustive list of all possible embodiments, applications or modifications of the invention. Thus, various modifications and variations of the described methods and systems of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are obvious to those skilled in molecular biology, immunology, chemistry, biochemistry or in the relevant fields are intended to be within the scope of the appended claims.

It is understood that the invention is not limited to the particular methodology, protocols, and reagents, etc., described herein, as these may vary as the skilled artisan will recognize. It is also to be understood that the terminology used herein is used for the purpose of describing particular embodiments only, and is not intended to limit the scope of the invention.

The embodiments of the invention and the various features and advantageous details thereof are explained more fully with reference to the non-limiting embodiments and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein.

Any numerical values recited herein include all values from the lower value to the upper value in increments of one unit provided that there is a separation of at least two units between any lower value and any higher value. As an example, if it is stated that the concentration of a component or value of a process variable such as, for example, size, angle size, pressure, time and the like, is, for example, from 1 to 90, specifically from 20 to 80, more specifically from 30 to 70, it is intended that values such as 15 to 85, 22 to 68, 43 to 51, 30 to 32, etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Particular methods, devices, and materials are described, although any methods and materials similar or equivalent to those described herein can be used in the practice or testing of the invention. The disclosures of all references and publications cited herein are expressly incorporated by reference in their entireties to the same extent as if each were incorporated by reference individually.

What is claimed is:

1. A method for determining an amount of N-terminal pro-Brain Natriuretic Peptide (NT-proBNP) in a sample from a canine, comprising determining an amount of a polypeptide consisting of GRSPASEASEASEASGLWAVQ (SEQ ID NO: 22) in the sample, and correlating the amount of the polypeptide in the sample to the amount of NT-proBNP in the sample.

2. The method of claim 1, wherein the step of determining the amount of the polypeptide comprises contacting the sample with a first antibody that specifically binds a first epitope on SEQ ID NO:22.

3. The method of claim 2, wherein the first antibody is a monoclonal antibody.

4. The method of claim 2, wherein the step of determining the amount of the polypeptide further comprises contacting the sample with a second antibody that specifically binds a second epitope on SEQ ID NO:22, wherein the first epitope is different than the second epitope.

5. The method of claim 4, wherein the second antibody is a monoclonal antibody.

6. The method of claim 4, wherein the first antibody is bound to a solid phase and the second antibody is bound to a label.

7. The method of claim 4, wherein the first antibody is bound to a label and the second antibody is bound to a solid phase.

8. The method according to claim 1, wherein the step of determining the amount of NT-proBNP comprises mass spectroscopy.

9. A method for determining a presence or an amount of canine N-terminal pro-Brain Natriuretic Peptide (NT-proBNP) in a biological sample comprising detecting a degradation product of NT-proBNP in the sample, wherein the degradation product consists of SEQ ID NO: 22.

10. The method of claim 9, wherein the step of detecting the degradation product comprises contacting the sample with a first antibody that specifically binds a first epitope on SEQ ID NO:22.

11. The method of claim 10, wherein the first antibody is a monoclonal antibody.

12. The method of claim 10, wherein the step of detecting the degradation product comprises contacting the sample with a second antibody that specifically binds a second epitope on SEQ ID NO:22, wherein the first epitope is different than the second epitope.

13. The method of claim 12, wherein the second antibody is a monoclonal antibody.

14. The method of claim 12, wherein the first antibody is bound to a solid phase and the second antibody is bound to a label.

15. The method of claim 12, wherein the first antibody is bound to a label and the second antibody is bound to a solid phase.

* * * * *

SEQUENCE LISTING

```
<160> NUMBER OF SEQ ID NOS: 42

<210> SEQ ID NO 1
<211> LENGTH: 140
<212> TYPE: PRT
<213> ORGANISM: Canis familiaris

<400> SEQUENCE: 1

Met Glu Pro Cys Ala Ala Leu Pro Arg Ala Leu Leu Leu Leu Leu Phe
1               5                   10                  15

Leu His Leu Ser Pro Leu Gly Gly Arg Pro His Pro Leu Gly Gly Arg
            20                  25                  30

Ser Pro Ala Ser Glu Ala Ser Glu Ala Ser Glu Ala Ser Gly Leu Trp
        35                  40                  45

Ala Val Gln Glu Leu Leu Gly Arg Leu Lys Asp Ala Val Ser Glu Leu
    50                  55                  60

Gln Ala Glu Gln Leu Ala Leu Glu Pro Leu His Arg Ser His Ser Pro
65                  70                  75                  80

Ala Glu Ala Pro Glu Ala Gly Gly Thr Pro Arg Gly Val Leu Ala Pro
                85                  90                  95

His Asp Ser Val Leu Gln Ala Leu Arg Arg Leu Arg Ser Pro Lys Met
            100                 105                 110

Met His Lys Ser Gly Cys Phe Gly Arg Arg Leu Asp Arg Ile Gly Ser
        115                 120                 125

Leu Ser Gly Leu Gly Cys Asn Val Leu Arg Lys Tyr
    130                 135                 140

<210> SEQ ID NO 2
<211> LENGTH: 132
<212> TYPE: PRT
<213> ORGANISM: Felis catus

<400> SEQUENCE: 2

Met Asp Pro Lys Thr Ala Leu Leu Arg Ala Leu Leu Leu Leu Leu Phe
1               5                   10                  15

Leu His Leu Ser Pro Leu Gly Gly Arg Ser His Pro Leu Gly Gly Pro
            20                  25                  30

Gly Pro Ala Ser Glu Ala Ser Ala Ile Gln Glu Leu Leu Asp Gly Leu
        35                  40                  45

Arg Asp Thr Val Ser Glu Leu Gln Glu Ala Gln Met Ala Leu Gly Pro
    50                  55                  60

Leu Gln Gln Gly His Ser Pro Ala Glu Ser Trp Glu Ala Gln Glu Glu
65                  70                  75                  80

Pro Pro Ala Arg Val Leu Ala Pro His Asp Asn Val Leu Arg Ala Leu
                85                  90                  95

Arg Arg Leu Gly Ser Ser Lys Met Met Arg Asp Ser Arg Cys Phe Gly
            100                 105                 110

Arg Arg Leu Asp Arg Ile Gly Ser Leu Ser Gly Leu Gly Cys Asn Val
        115                 120                 125
```

```
Leu Arg Arg His
    130

<210> SEQ ID NO 3
<211> LENGTH: 134
<212> TYPE: PRT
<213> ORGANISM: Homo sapiens

<400> SEQUENCE: 3

Met Asp Pro Gln Thr Ala Pro Ser Arg Ala Leu Leu Leu Leu Leu Phe
1               5                   10                  15

Leu His Leu Ala Phe Leu Gly Gly Arg Ser His Pro Leu Gly Ser Pro
            20                  25                  30

Gly Ser Ala Ser Asp Leu Glu Thr Ser Gly Leu Gln Glu Gln Arg Asn
        35                  40                  45

His Leu Gln Gly Lys Leu Ser Glu Leu Gln Val Glu Gln Thr Ser Leu
    50                  55                  60

Glu Pro Leu Gln Glu Ser Pro Arg Pro Thr Gly Val Trp Lys Ser Arg
65                  70                  75                  80

Glu Val Ala Thr Glu Gly Ile Arg Gly His Arg Lys Met Val Leu Tyr
                85                  90                  95

Thr Leu Arg Ala Pro Arg Ser Pro Lys Met Val Gln Gly Ser Gly Cys
            100                 105                 110

Phe Gly Arg Lys Met Asp Arg Ile Ser Ser Ser Ser Gly Leu Gly Cys
        115                 120                 125

Lys Val Leu Arg Arg His
    130

<210> SEQ ID NO 4
<211> LENGTH: 79
<212> TYPE: PRT
<213> ORGANISM: Artificial Sequence
<220> FEATURE:
<223> OTHER INFORMATION: Synthetic

<400> SEQUENCE: 4

His Pro Leu Gly Gly Arg Ser Pro Ala Ser Glu Ala Ser Glu Ala Ser
1               5                   10                  15

Glu Ala Ser Gly Leu Trp Ala Val Gln Glu Leu Leu Gly Arg Leu Lys
            20                  25                  30

Asp Ala Val Ser Glu Leu Gln Ala Glu Gln Leu Ala Leu Glu Pro Leu
        35                  40                  45

His Arg Ser His Ser Pro Ala Glu Ala Pro Glu Ala Gly Gly Thr Pro
    50                  55                  60

Arg Gly Val Leu Ala Pro His Asp Ser Val Leu Gln Ala Leu Arg
65                  70                  75

<210> SEQ ID NO 5
<211> LENGTH: 6
<212> TYPE: PRT
<213> ORGANISM: Canis familiaris

<400> SEQUENCE: 5

His Pro Leu Gly Gly Arg
1               5

<210> SEQ ID NO 6
<211> LENGTH: 24
<212> TYPE: PRT
```

<213> ORGANISM: Canis familiaris

<400> SEQUENCE: 6

Ser Pro Ala Ser Glu Ala Ser Glu Ala Ser Gly Leu Trp
1               5                   10                  15
Ala Val Gln Glu Leu Leu Gly Arg
            20

<210> SEQ ID NO 7
<211> LENGTH: 18
<212> TYPE: PRT
<213> ORGANISM: Canis familiaris

<400> SEQUENCE: 7

Asp Ala Val Ser Glu Leu Gln Ala Glu Gln Leu Ala Leu Glu Pro Leu
1               5                   10                  15
His Arg

<210> SEQ ID NO 8
<211> LENGTH: 15
<212> TYPE: PRT
<213> ORGANISM: Canis familiaris

<400> SEQUENCE: 8

Ser His Ser Pro Ala Glu Ala Pro Glu Ala Gly Gly Thr Pro Arg
1               5                   10                  15

<210> SEQ ID NO 9
<211> LENGTH: 14
<212> TYPE: PRT
<213> ORGANISM: Canis familiaris

<400> SEQUENCE: 9

Gly Val Leu Ala Pro His Asp Ser Val Leu Gln Ala Leu Arg
1               5                   10

<210> SEQ ID NO 10
<211> LENGTH: 6
<212> TYPE: PRT
<213> ORGANISM: Canis familiaris

<400> SEQUENCE: 10

Gly Gly Arg Ser Pro Ala
1               5

<210> SEQ ID NO 11
<211> LENGTH: 7
<212> TYPE: PRT
<213> ORGANISM: Canis familiaris

<400> SEQUENCE: 11

His Arg Ser His Ser Pro Ala
1               5

<210> SEQ ID NO 12
<211> LENGTH: 4
<212> TYPE: PRT
<213> ORGANISM: Canis familiaris

<400> SEQUENCE: 12

Pro Arg Gly Val
1

```
<210> SEQ ID NO 13
<211> LENGTH: 5
<212> TYPE: PRT
<213> ORGANISM: Canis familiaris

<400> SEQUENCE: 13

Pro His Asp Ser Val
1               5

<210> SEQ ID NO 14
<211> LENGTH: 28
<212> TYPE: PRT
<213> ORGANISM: Canis familiaris

<400> SEQUENCE: 14

Leu Gly Gly Arg Ser Pro Ala Ser Glu Ala Ser Glu Ala Ser Glu Ala
1               5                   10                  15

Ser Gly Leu Trp Ala Val Gln Glu Leu Leu Gly Arg
            20                  25

<210> SEQ ID NO 15
<211> LENGTH: 23
<212> TYPE: PRT
<213> ORGANISM: Canis familiaris

<400> SEQUENCE: 15

Leu Gly Gly Arg Ser Pro Ala Ser Glu Ala Ser Glu Ala Ser Glu Ala
1               5                   10                  15

Ser Gly Leu Trp Ala Val Gln
            20

<210> SEQ ID NO 16
<211> LENGTH: 25
<212> TYPE: PRT
<213> ORGANISM: Canis familiaris

<400> SEQUENCE: 16

Leu Gly Gly Arg Ser Pro Ala Ser Glu Ala Ser Glu Ala Ser Glu Ala
1               5                   10                  15

Ser Gly Leu Trp Ala Val Gln Glu Leu
            20                  25

<210> SEQ ID NO 17
<211> LENGTH: 26
<212> TYPE: PRT
<213> ORGANISM: Canis familiaris

<400> SEQUENCE: 17

Leu Gly Gly Arg Ser Pro Ala Ser Glu Ala Ser Glu Ala Ser Glu Ala
1               5                   10                  15

Ser Gly Leu Trp Ala Val Gln Glu Leu Leu
            20                  25

<210> SEQ ID NO 18

<400> SEQUENCE: 18

000

<210> SEQ ID NO 19
<211> LENGTH: 22
<212> TYPE: PRT
<213> ORGANISM: Canis familiaris
```

```
<400> SEQUENCE: 19

Gly Gly Arg Ser Pro Ala Ser Glu Ala Ser Glu Ala Ser Glu Ala Ser
1               5                   10                  15

Gly Leu Trp Ala Val Gln
            20

<210> SEQ ID NO 20
<211> LENGTH: 25
<212> TYPE: PRT
<213> ORGANISM: Canis familiaris

<400> SEQUENCE: 20

Gly Gly Arg Ser Pro Ala Ser Glu Ala Ser Glu Ala Ser Glu Ala Ser
1               5                   10                  15

Gly Leu Trp Ala Val Gln Glu Leu Leu
            20                  25

<210> SEQ ID NO 21
<211> LENGTH: 28
<212> TYPE: PRT
<213> ORGANISM: Canis familiaris

<400> SEQUENCE: 21

Gly Gly Arg Ser Pro Ala Ser Glu Ala Ser Glu Ala Ser Glu Ala Ser
1               5                   10                  15

Gly Leu Trp Ala Val Gln Glu Leu Leu Gly Arg Leu
            20                  25

<210> SEQ ID NO 22
<211> LENGTH: 21
<212> TYPE: PRT
<213> ORGANISM: Canis familiaris

<400> SEQUENCE: 22

Gly Arg Ser Pro Ala Ser Glu Ala Ser Glu Ala Ser Glu Ala Ser Gly
1               5                   10                  15

Leu Trp Ala Val Gln
            20

<210> SEQ ID NO 23
<211> LENGTH: 25
<212> TYPE: PRT
<213> ORGANISM: Canis familiaris

<400> SEQUENCE: 23

Gly Arg Ser Pro Ala Ser Glu Ala Ser Glu Ala Ser Glu Ala Ser Gly
1               5                   10                  15

Leu Trp Ala Val Gln Glu Leu Leu Gly
            20                  25

<210> SEQ ID NO 24
<211> LENGTH: 48
<212> TYPE: PRT
<213> ORGANISM: Canis familiaris

<400> SEQUENCE: 24

Leu Trp Ala Val Gln Glu Leu Leu Gly Arg Leu Lys Asp Ala Val Ser
1               5                   10                  15

Glu Leu Gln Ala Glu Gln Leu Ala Leu Glu Pro Leu His Arg Ser His
            20                  25                  30

Ser Pro Ala Glu Ala Pro Glu Ala Gly Gly Thr Pro Arg Gly Val Leu
```

```
                    35                  40                  45
```

<210> SEQ ID NO 25
<211> LENGTH: 13
<212> TYPE: PRT
<213> ORGANISM: Canis familiaris

<400> SEQUENCE: 25

Glu Leu Leu Gly Arg Leu Lys Asp Ala Val Ser Glu Leu
1               5                   10

<210> SEQ ID NO 26
<211> LENGTH: 13
<212> TYPE: PRT
<213> ORGANISM: Canis familiaris

<400> SEQUENCE: 26

Leu Lys Asp Ala Val Ser Glu Leu Gln Ala Glu Gln Leu
1               5                   10

<210> SEQ ID NO 27
<211> LENGTH: 8
<212> TYPE: PRT
<213> ORGANISM: Canis familiaris

<400> SEQUENCE: 27

Glu Gln Leu Ala Leu Glu Pro Leu
1               5

<210> SEQ ID NO 28
<211> LENGTH: 5
<212> TYPE: PRT
<213> ORGANISM: Canis familiaris

<400> SEQUENCE: 28

Ala Leu Glu Pro Leu
1               5

<210> SEQ ID NO 29

<400> SEQUENCE: 29

000

<210> SEQ ID NO 30
<211> LENGTH: 26
<212> TYPE: PRT
<213> ORGANISM: Canis familiaris

<400> SEQUENCE: 30

Ser His Ser Pro Ala Glu Ala Pro Glu Ala Gly Gly Thr Pro Arg Gly
1               5                   10                  15

Val Leu Ala Pro His Asp Ser Val Leu Gln
            20                  25

<210> SEQ ID NO 31
<211> LENGTH: 11
<212> TYPE: PRT
<213> ORGANISM: Canis familiaris

<400> SEQUENCE: 31

Gly Val Leu Ala Pro His Asp Ser Val Leu Gln
1               5                   10

```
<210> SEQ ID NO 32
<211> LENGTH: 21
<212> TYPE: PRT
<213> ORGANISM: Canis familiaris
<220> FEATURE:
<221> NAME/KEY: MISC_FEATURE
<222> LOCATION: (25)..(25)
<223> OTHER INFORMATION: (PEG)6-Cys-KLH

<400> SEQUENCE: 32

Gly Arg Ser Pro Ala Ser Glu Ala Ser Glu Ala Ser Glu Ala Ser Gly
1               5                   10                  15

Leu Trp Ala Val Gln
            20

<210> SEQ ID NO 33
<211> LENGTH: 21
<212> TYPE: PRT
<213> ORGANISM: Canis familiaris
<220> FEATURE:
<221> NAME/KEY: MISC_FEATURE
<222> LOCATION: (1)..(1)
<223> OTHER INFORMATION: KLH-Cys-(PEG)6

<400> SEQUENCE: 33

Gly Arg Ser Pro Ala Ser Glu Ala Ser Glu Ala Ser Glu Ala Ser Gly
1               5                   10                  15

Leu Trp Ala Val Gln
            20

<210> SEQ ID NO 34
<211> LENGTH: 26
<212> TYPE: PRT
<213> ORGANISM: Canis familiaris
<220> FEATURE:
<221> NAME/KEY: MISC_FEATURE
<222> LOCATION: (26)..(26)
<223> OTHER INFORMATION: (PEG)6-Cys-KLH

<400> SEQUENCE: 34

Ser His Ser Pro Ala Glu Ala Pro Glu Ala Gly Gly Thr Pro Arg Gly
1               5                   10                  15

Val Leu Ala Pro His Asp Ser Val Leu Gln
            20                  25

<210> SEQ ID NO 35
<211> LENGTH: 26
<212> TYPE: PRT
<213> ORGANISM: Canis familiaris
<220> FEATURE:
<221> NAME/KEY: MISC_FEATURE
<222> LOCATION: (1)..(1)
<223> OTHER INFORMATION: KLH-Cys-(PEG)6

<400> SEQUENCE: 35

Ser His Ser Pro Ala Glu Ala Pro Glu Ala Gly Gly Thr Pro Arg Gly
1               5                   10                  15

Val Leu Ala Pro His Asp Ser Val Leu Gln
            20                  25

<210> SEQ ID NO 36
<211> LENGTH: 20
<212> TYPE: PRT
<213> ORGANISM: Canis familiaris

<400> SEQUENCE: 36
```

-continued

```
Leu Lys Asp Ala Val Ser Glu Leu Gln Ala Glu Gln Leu Ala Leu Glu
1               5                   10                  15

Pro Leu His Arg
            20

<210> SEQ ID NO 37
<211> LENGTH: 17
<212> TYPE: PRT
<213> ORGANISM: Canis familiaris

<400> SEQUENCE: 37

Lys Asp Ala Val Ser Glu Leu Gln Ala Glu Gln Leu Ala Leu Glu Pro
1               5                   10                  15

Leu

<210> SEQ ID NO 38

<400> SEQUENCE: 38

000

<210> SEQ ID NO 39

<400> SEQUENCE: 39

000

<210> SEQ ID NO 40
<211> LENGTH: 13
<212> TYPE: PRT
<213> ORGANISM: Canis familiaris

<400> SEQUENCE: 40

His Pro Leu Gly Gly Arg Ser Pro Ala Ser Glu Ala Ser
1               5                   10

<210> SEQ ID NO 41
<211> LENGTH: 6
<212> TYPE: PRT
<213> ORGANISM: Canis familiaris

<400> SEQUENCE: 41

Asp Ala Val Ser Glu Leu
1               5

<210> SEQ ID NO 42
<211> LENGTH: 4
<212> TYPE: PRT
<213> ORGANISM: Canis familiaris

<400> SEQUENCE: 42

Leu Glu Pro Leu
1
```